United States Patent [19]

Arndt et al.

[11] Patent Number: 5,159,074
[45] Date of Patent: Oct. 27, 1992

[54] AMINOMETHANEPHOSPHONIC ACID ARYL ESTERS, A PROCESS FOR THEIR PRODUCTION AND THEIR USE

[75] Inventors: Uwe Arndt, Cologne; Hans-Dieter Block, Leverkusen; Wolfgang-Hans Schulz-Schlitte, Dormagen, all of Fed. Rep. of Germany

[73] Assignee: Bayer Aktiengesellschaft, Leverkusen, Fed. Rep. of Germany

[21] Appl. No.: 588,914

[22] Filed: Sep. 27, 1990

[30] Foreign Application Priority Data

Oct. 7, 1989 [DE] Fed. Rep. of Germany ....... 3933546

[51] Int. Cl.$^5$ ..................... C07D 251/70; C09D 5/18
[52] U.S. Cl. .................................. 544/195; 106/18.15
[58] Field of Search ......................................... 544/195

[56] References Cited

FOREIGN PATENT DOCUMENTS 2042661 3/1972 Fed. Rep. of Germany .
2315212 10/1973 Fed. Rep. of Germany .

Primary Examiner—Marianne Cintins
Assistant Examiner—Michael B. Hydorn
Attorney, Agent, or Firm—Sprung Horn Kramer & Woods

[57] ABSTRACT

Aminomethanephosphonic acid aryl esters of the formula

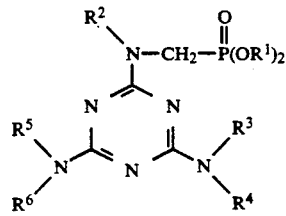

in which $R^1$ is an aromatic radical and $R^2$, $R^3$, $R^4$, $R^5$ and $R^6$ independently of one another represent hydrogen atoms,

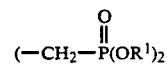

groups, an optionally substituted $C_{1-10}$ alkyl radical or an optionally substituted aromatic ring, or salts thereof.

These aminomethanephosphonic acid aryl esters are useful as flameproofing agents in foams, thermoplastics and thermosets and as a crosslinking component in oligo-and polycondensates based on monomers containing hydroxy groups.

10 Claims, No Drawings

AMINOMETHANEPHOSPHONIC ACID ARYL ESTERS, A PROCESS FOR THEIR PRODUCTION AND THEIR USE

This invention relates to aminomethanephosphonic acid aryl esters of melamine, to a process for their production and to their use as flameproofing agents and as a crosslinking component in oligo- and polycondensates based on monomers containing hydroxy groups.

Phosphorus-containing compounds and especially phosphonic acid esters are used as effective flameproofing agents in foams, thermoplastics and thermosets. A phosphorus-containing compound typically used for this purpose is dimethyl methyl phosphonate (DMMP), as described in EP 0 108 713. However, the use of DMMP involves difficulties.

Firstly, dimethyl methyl phosphonate is a relatively volatile liquid (melting point 181 C), so that the material can be lost by volatilization, particularly at elevated temperatures. Secondly, dimethyl methyl phosphonate, like most phosphonic acid esters of lower aliphatic alcohols, has an alkylating effect in the presence of alkylatable substances, such as amine for example.

EP 0 149 480 describes the use of phosphonic acid salts of methanephosphonic acid which have fewer of the above-mentioned disadvantages. However, salt-like flameproofing agents cannot be used without some compromise in many fields of application, for example in thermoplastics used in the electrical field.

The problem addressed by the present invention was to provide a class of compounds which showed reduced volatility in relation to the classes mentioned above and, at the same time, a good flameproofing effect.

According to the invention, this problem is solved by the synthesis of aminomethanephosphonic acid aryl esters corresponding to general formula (I)

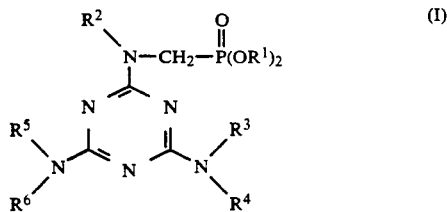

in which $R^1$ is an aromatic radical and $R^2$, $R^3$, $R^4$, $R^5$ and $R^6$ independently of one another represent hydrogen atoms,

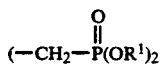

groups, an optionally substituted $C_{1-10}$ alkyl radical or an optionally substituted aromatic ring, or salts thereof.

Salts of the aminomethanephosphonic acid aryl esters corresponding to general formula (I) may be obtained by quaternization of individual nitrogen atoms or several nitrogen atoms by alkylating substances, such as for example alkyl iodides or phosphorous acid esters or phosphonic acid esters of lower aliphatic alcohols, or by partial saponification of individual ester groups or several ester groups.

Suitable aromatic radicals are, for example, phenyl radicals or substituted phenyl radicals, such as for example the alkyl-substituted isomeric methyl and dimethyl phenyl radicals, the isomeric mono- and diethyl phenyl radicals, the isomeric mono- and diisopropyl phenyl radicals, the isomeric mono- and ditert.-butyl phenyl radicals, i-octyl phenyl, nonyl phenyl, phenyl phenyl, isopropylphenyl phenyl, dodecyl phenyl, phenylmethylene phenyl, phenylisopropylidene phenyl or cyclohexyl phenyl, or halogen-substituted phenyl radicals, such as for example the isomeric mono- and dichlorophenyl radicals, the isomeric mono- and dibromophenyl radicals, or amino-substituted phenyl radicals, such as aminophenyl for example, or mixed-substituted phenyl radicals.

The optionally substituted $C_{1-10}$ alkyl radical may be selected from unsubstituted and unbranched alkyl radicals, such as methyl, ethyl, n-propyl, n-butyl, etc. and their isomeric forms, such as i-propyl, i-butyl, tert.-butyl, etc.; the substituted alkyl radicals may be selected from mono- or polyhydroxy-substituted unbranched and branched radicals, such as for example the —CH$_2$—OH radical, the —CH$_2$CH$_2$—OH radical, the —CH$_2$—CH$_2$—CH$_2$—OH radical, the —CH$_2$—CH(OH)—CH$_3$ radical, the —CH$_2$—CH(OH)—C$_2$H$_5$ radical, the —CH$_2$—CH(OH)—CH$_2$—Cl radical, mono- or polyamino-substituted unbranched or branched radicals, such as for example the —CH$_2$—NH$_2$ radical, the —CH$_2$—CH$_2$—NH$_2$ radical, the —CH$_2$—CH$_2$—CH$_2$—NH$_2$— radical, the —CH$_2$—CH(NH$_2$)—CH$_3$ radical, and iminosubstituted radicals and halogen-substituted alkyl radicals and also mixed-substituted alkyl radicals.

Preferred aminomethane phosphonic acid aryl esters are those in which the optionally substituted $C_{1-10}$ alkyl radical is a —CH$_2$—OH group.

Aminomethane phosphonic acid aryl esters, in which $R^3$ and $R^5$ represent

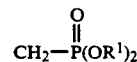

groups and $R^2$, $R^4$ and $R^6$ independently of one another represent —H atoms or —CH$_2$OH groups, are particularly preferred.

The present invention also relates to a process for the production of aminomethanephosphonic acid aryl esters corresponding to general formula I by reaction of an optionally substituted melamine derivative corresponding to general formula (II)

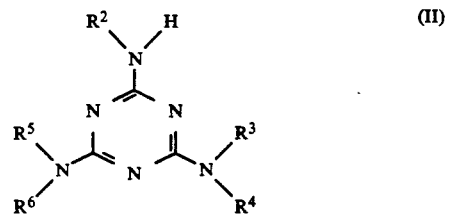

in which $R^2$, $R^3$, $R^4$, $R^5$ and $R^6$ are as defined above, with a triaryl phosphite corresponding to the following general formula

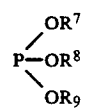

in which $R^7$, $R^8$ and $R^9$ may be the same or different and represent aromatic radicals, in a molar ratio of 0.01 to 100 mol-%, based on the —N-H functions present, and with paraformaldehyde in a ratio of 100 to 600 mol-% paraformaldehyde, based on triaryl phosphite, at temperatures in the range from 20° to 300° C.

The quantity of paraformaldehyde to be used may also be introduced in the form of gaseous formaldehyde.

Reactions in which the triaryl phosphite is used in a substoichiometric quantity, based on all the N-H functions present, are particularly advantageous.

The reactions are preferably conducted at temperatures in the range from 90° to 160° C.

Processes in which triphenyl phosphite is used as the triaryl phosphite and unsubstituted melamine is used as the melamine derivative are particularly preferred.

The optionally substituted melamine, the triaryl phosphite and the paraformaldehyde may be reacted with one another in a single-stage reaction.

In one particularly favorable variant of the process, the optionally substituted melamine and the triaryl phosphite are initially introduced and the paraformaldehyde is added afterwards.

The aminomethanephosphonic acid aryl esters according to the invention are eminently suitable for use as flameproofing agents in foams, such as for example polyurethane foams and polyisocyanurate foams and polycarbodiimide foams based on isocyanates or carbodiimides, thermoplastics, such as for example polyethylene terephthalate, polybutylene terephthalate, polyamide 6, polyamide 6.6, polycarbonate, polyvinyl chloride, polyacrylonitrile, polyacrylate, polymethacrylate, polybutadiene, polystyrene and also copolymers and co-condensates of various monomers and blends of various thermoplastics, such as for example a polycarbonate/acrylonitrile-butadiene/styrene blend, and thermosets, such as for example phenol-formaldehyde resins based on unsubstituted phenol, cresol, xylenol and higher homologous phenols, or formaldehyde resins based on aliphatic and aromatic amines, such as for example urea, thiourea, dicyanodiamide, melamine and the isomeric phenylenediamines, or resins based on epoxides and unsaturated polyester resins based, for example, on maleic acid, phthalic acid, diols and styrene, optionally in combination with other flameproofing agents, such as for example triaryl phosphates, such as triphenyl phosphate, diphenyl cresyl phosphate, tricresyl phosphate, the isomeric isopropylphenyl phenyl phosphates, the isomeric tert.-butylphenyl phenyl phosphates, the isomeric α-methylbenzylphenyl phenyl phosphates, or trialkyl phosphates, such as for example triethyl phosphate, trichloroethyl phosphate, trichloropropyl phosphate, tris-dichloropropyl phosphate, ethylene glycol bis-di-2-chloroethyl phosphate, ethylene glycol bis-di-2-chloroethyl phosphate, bis-chloromethyl propanediol bis-di-2-chloroethyl phosphate, bis-chloromethyl propanediol bis-di-2-chloroethyl phosphate, or phosphonic acid esters, such as for example methanephosphonic acid dimethyl ester, methanephosphonic acid diphenyl ester, benzenephosphonic acid diphenyl ester, or phosphinic acid esters, such as for example 1-methoxy-1-oxophospholene, 1-ethoxy-1-oxophospholene, 1-propoxy-1-oxophospholene, 1-phenoxy-1-oxophospholene, or phosphine oxides, such as for example 1-methyl-1-oxophospholene and triphenyl phosphane oxide, or aliphatic and aromatic phosphanes, such as for example tributyl phosphane or triphenyl phosphane, salts of these compounds and combinations of these compounds. The aminomethanephosphonic acid aryl esters according to the invention are also eminently suitable as a crosslinking component in oligo- and polycondensates based on monomers containing hydroxy groups.

The compounds according to the invention are generally prepared as follows:

The melamine or melamine derivative to be substituted is contacted with a triaryl phosphite in a molar ratio of 0.01 to 100 mol-% per —N-H function present and with paraformaldehyde in a molar ratio of 100 to 600 mol-%, based on the triaryl phosphite used, at temperatures in the range from 20° to 300° C. After volatile constituents have been distilled off on completion of the reaction, the compounds according to the invention may be used in accordance with the invention, optionally after purification by washing.

In one preferred embodiment, the compounds according to the invention are prepared as follows:

The quantities of melamine or melamine derivative and triaryl phosphite to be used in accordance with the desired product composition are introduced into a stirred reaction vessel and heated to 140°-150° C. The quantity of paraformaldehyde to be used in accordance with the desired product composition is gradually introduced at that temperature. After the addition and on completion of the reaction, the volatile constituents are distilled off in vacuo.

The invention is illustrated by the following Examples, in which purity data are expressed as phosphorus unless otherwise shown.

EXAMPLES

Example 1

(N-diphenoxyphosphomethyl)-melamine

The reaction of 31.5 g (0.25 mol) melamine, 77.5 g (0.25 mol) triphenyl phosphite and 9.9 g (0.33 mol) paraformaldehyde as described above, followed by the removal of 23 g volatile products by distillation at a temperature of 150° C. under a pressure of 2 mbar, gives 90 g product, corresponding to a yield of 96.8%, with a purity of greater than 90% (as determined by : P-NMR)

EXAMPLE 2

The reaction of 31.5 g (0.25 mol) melamine, 232.5 g (0.75 mol) triphenyl phosphite and 30.0 g (1.00 mol) paraformaldehyde as described above, followed by the removal of 23 g volatile products by distillation at a temperature of 150° C under a pressure of 2 mbar, gives 203 g product, corresponding to a yield of 94%, with a purity of greater than 90% (as determined by $^{31}$P-NMR, sum of all the isomers).

EXAMPLE 3

The reaction of 31.5 g (0.25 mol) melamine, 465.0 g (1.50 mol) triphenyl phosphite and 59.3 g (1.98 mol) paraformaldehyde as described above, followed by the removal of 23 g volatile products by distillation at a temperature of 150° C. under a pressure of 2 mbar, gives 965 g product, corresponding to a yield of 91%, with a purity of greater than 85% (as determined by $^{31}$P-NMR).

It will be appreciated that the instant specification and claims are set forth by way of illustration and not limitation, and that various modifications and changes may be made without departing from the spirit and scope of the present invention.

What is claimed is:

1. An aminomethanephosphonic acid aryl ester of the formula

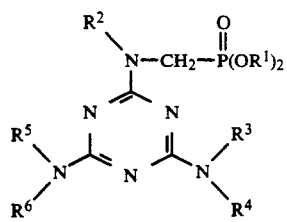

(I)

wherein

R$^1$ represents phenyl or phenyl substituted by one or more substituents independently selected from the group consisting of alkyl, phenyl, isopropylphenyl, phenylmethylene, phenylisopropylidene, cyclohexyl, halogen, or amino; and R$^2$, R$^3$, R$^4$, R$^5$ and R$^6$ are independently selected from the group consisting of hydrogen; —CH$_2$—PO(OR$^1$)$_2$; alkyl or alkyl substituted by one or more substituents independently selected from the group consisting of hydroxy, amino, imino, and halogen; and phenyl or phenyl substituted by one or more substituents independently selected form the group consisting of alkyl, phenyl, isopropylphenyl, phenylmethylene, phenylisopropylidene, cyclohexyl, halogen, or amino; or salts thereof.

2. An aminomethanephosphonic acid aryl ester according to claim 1, wherein R$^2$, R$^3$, R$^4$, R$^5$ and R$^6$ are independently selected form the group consisting of hydrogen, —CH$_2$—PO(OR$^1$)$_2$, —CH$_2$—OH, phenyl, methylphenyl, dimethylphenyl, ethylphenyl, diethylphenyl, isopropylphenyl, diisopropylphenyl, tert.-butylphenyl, di-tert.-butylphenyl, ioctylphenyl, nonylphenyl, phenylphenyl, isopropylphenylphenyl, dodecylphenyl, phenylmethylenephenyl, phenylisopropylidenephenyl, cyclohexylphenyl, chlorophenyl, dichlorophenyl, bromophenyl, dibromophenyl, and aminophenyl.

3. An aminomethanephosphonic acid aryl ester according to claim 1, wherein R$^3$ and R$^5$ represent

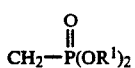

groups and R$^2$, R$^4$, and R$^6$ independently of one another represent —H atoms of —CH$_2$OH groups, and A' is defined as in claim 1.

4. A process for the production of an aminomethanephosphonic acid aryl ester according to claim 1, comprising reacting a melamine of the formula

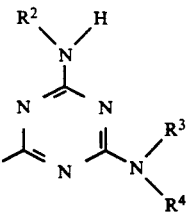

with a triaryl phosphite of the formula

in which R$^7$, R$^8$, and R$^9$ may be the same or different and represent aromatic radicals, in a molar ratio of 0.01 to 100 mol-%, based on the —N-H functions present, and with paraformaldehyde in a ratio of 100 to 600 mol-% paraformaldehyde, based on triaryl phosphite, at temperatures in the range from 20 to 300° C., and R$^2$, R$^3$, R$^4$, R$^5$ and R$^6$ R$^2$, R$^3$, R$^4$, R$^5$ and R$^6$ are defined as in claim 1.

5. A process according to claim 4, wherein the triaryl phosphite is used in a substoichiometric quantity, based on all the N—H functions present.

6. A process according to claim 4, wherein the triaryl phosphite is triphenyl phosphite and unsubstituted melamine is used as the melamine.

7. A process according to claim 4, wherein the melamine the triaryl phosphite and the paraformaldehyde are reacted in a single-stage reaction.

8. A process according to claim 4, wherein the melamine and the triaryl phosphite are initially introduced and the paraformaldehyde is added afterwards.

9. The aminomethanephosphonic acid aryl ester according to claim 1, wherein

R$^1$ represents phenyl, methylphenyl, dimethylphenyl, ethylphenyl, diethylphenyl, isopropylphenyl, diisopropylphenyl, tert.-butylphenyl, di-tert.-butylphenyl, i-octylphenyl, nonphenyl, phenylphenyl, isopropylphenylphenyl, dodecylphenyl, phenylmethylenephenyl, phenylisopropylidenephenyl, cyclohexylphenyl, chlorophenyl, dichlorophenyl, bromophenyl, dibromophenyl, or aminophenyl; and R$^2$, R$^3$, R$^4$, R$^5$ and R$^6$ are independently selected from the group consisting of hydrogen, —CH$_2$—PO(OR$^1$)$_2$, methyl, ethyl, n-propyl, n-butyl, i-propyl, i-butyl, tert.-butyl, —CH$_2$—OH, —CH$_2$—CH$_2$—OH, —CH$_2$—CH(OH)—CH$_3$, —CH$_2$—CH(OH)—C$_2$H$_5$, —CH$_2$—CH(OH)—CH$_2$—Cl, —CH$_2$—NH$_2$, —CH$_2$—CH$_2$—NH$_2$, —CH$_2$—CH$_2$—CH$_2$—NH$_2$, —CH$_2$—CH(NH$_2$)—CH$_3$, phenyl, methylphenyl, dimethylphenyl, ethylphenyl, diethylphenyl, isopropylphenyl, diisopropylphenyl, tert.-butylphenyl, di-tert.-butylphenyl, i-octylphenyl, nonylphenyl, phenylphenyl, isopropylphenylphenyl, dodecylphenyl, phenylmethylenephenyl, phenylisopropylidenephenyl, cyclohexylphenyl, chlorophenyl, dichlorophenyl, bromophenyl, dibromophenyl, and aminophenyl; or salts thereof.

10. The aminomethanephosphonic acid aryl ester according to claim 1, which is (N-diphenoxyphosphomethyl)-melamine.

* * * * *

UNITED STATES PATENT AND TRADEMARK OFFICE
CERTIFICATE OF CORRECTION

PATENT NO. : 5,159,074

DATED : October 27, 1992

INVENTOR(S) : Arndt, et al.

It is certified that error appears in the above-identified patent and that said Letters Patent is hereby corrected as shown below:

Col. 5, line 62  Delete " of " and substitute -- or --; delete " A' " and substitute -- R' --

Col. 6, line 52  After " -$CH_2$-OH, " insert -- -$CH_2$-$CH_2$-OH, --

Signed and Sealed this

Twenty-second Day of March, 1994

Attest:

BRUCE LEHMAN

Attesting Officer      Commissioner of Patents and Trademarks